United States Patent [19]

Smith

[11] 4,224,255

[45] Sep. 23, 1980

[54] PROCESS FOR THE PRODUCTION OF ALDEHYDES AND ALCOHOLS FROM OLEFINICALLY UNSATURATED COMPOUNDS BY HYDROFORMYLATION WITH SUPPRESSION OF OLEFIN HYDROGENATION

[75] Inventor: William E. Smith, Schenectady, N.Y.

[73] Assignee: General Electric Company, Pittsfield, Mass.

[21] Appl. No.: 915,767

[22] Filed: Jun. 15, 1978

[51] Int. Cl.$^2$ ............................................. C07C 45/10
[52] U.S. Cl. ................................... 568/451; 568/909; 568/454
[58] Field of Search ............... 260/599, 604 HF, 602, 260/601 R, 601; 568/909

[56] References Cited

U.S. PATENT DOCUMENTS

| | | | |
|---|---|---|---|
| 3,239,566 | 3/1966 | Slaugh et al. | 260/604 HF |
| 3,274,263 | 9/1966 | Greene et al. | 260/632 HF |
| 3,825,601 | 7/1974 | Rennick | 260/604 HF |
| 3,917,661 | 11/1975 | Pruett et al. | 260/410.9 R |

Primary Examiner—Werren B. Lone
Attorney, Agent, or Firm—Morgan, Finnegan, Pine, Foley & Lee

[57] ABSTRACT

Oxygenated compounds are prepared by reacting olefinically unsaturated compounds with carbon monoxide and hydrogen in the presence of a hydroformylation catalyst with suppression of the olefin hydrogenation side reaction if an acid is used in the reaction mixture. Typically, o-phthalic acid suppresses the formation of hexane and n-propanol, respectively, when 1-hexene and allyl alcohol are hydroformylated.

18 Claims, No Drawings

PROCESS FOR THE PRODUCTION OF ALDEHYDES AND ALCOHOLS FROM OLEFINICALLY UNSATURATED COMPOUNDS BY HYDROFORMYLATION WITH SUPPRESSION OF OLEFIN HYDROGENATION

The present invention relates to an improved preparation of oxygenated organic compounds from olefinically unsaturated compounds, carbon monoxide and hydrogen. More particularly, it relates to a process for hydroformylating olefinic compounds, while at the same time suppressing olefin hydrogenation by using an acid to suppress the side reaction.

BACKGROUND OF THE INVENTION

Processes for producing oxygenated products, e.g., aldehydes and/or alcohols, by reaction of olefinically unsaturated compounds with carbon monoxide and hydrogen at elevated temperatures and pressures in the presence of certain catalysts are well known in the art. The aldehydes and alcohols so produced are useful per se and also as intermediates in the production of other valuable compounds. The oxygenated compounds generally correspond to addition of a carbonyl or carbinol grouping to the starting material with simultaneous saturation of the olefin bond. Such processes are generally known under varying names, such as the Oxo-process or the hydroformylation process.

Incorporated herein for background purposes are Pruett et al, U.S. Pat. No. 3,917,661, which deals generally with the hydroformylation of unsaturated organic compounds and Slaugh et al, U.S. Pat. No. 3,239,566, which deals specifically with the hydroformylation of olefins.

A substantial disadvantage in prior art hydroformylation processes is the formation, by a side reaction, of by-products based on hydrogenation rather than hydroformylation of the olefin bond. In commercial experience, substantial amounts of the olefinically unsaturated substrates are simply converted to nearly useless hydrogenation products, instead of the desired oxygenated compounds. A means to suppress or reduce substrate hydrogenation in such processes and the economic value of such a discovery is self-evident. Such a means is the subject of the present invention.

In essence, the present invention comprises the addition of an acidic compound to the hydroformylation reaction mixture, in an amount at least sufficient to suppress substrate hydrogenation. A preferred acid for this purpose is phthalic acid and related compounds.

The use of phthalic acid and related compounds as co-catalysts in the rhodium carbonyl catalyzed hydroformylation of allyl alcohol or its homologs is described in another context applicant's co-pending U.S. patent application, Ser. No. 849,435, filed Nov. 7, 1977. By way of illustration, phthalic acid and related compounds are shown therein to be particularly effective as co-catalysts (used in conjunction with the rhodium carbonyl/triarylphosphine combination) for the oxo tetrahydrofuranylation process. The designed purpose of the phthalic acid in that process was promotion of the conversion of the 2-hydroxytetrahydrofuran intermediate to a stable 2-alkoxytetrahydrofuran (Equation 1).

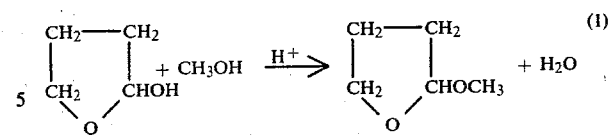

The phthalic acid has a somewhat rate-retarding effect on the hydroformylation reaction (allyl alcohol) itself, but no particular benefits or deleterious effects in that step of this relatively complicated system were perceived.

With a simpler system, however, a dramatic positive consequence of using the phthalic acid catalyst component in the hydroformylation reaction has been discovered. Application of the phthalic acid/triphenylphosphine/rhodium carbonyl catalyst to the hydroformylation of conventional olefins demonstrates an unprecedented effect—the substrate hydrogenation side reaction characteristic of the Oxo process can be virtually completely suppressed with this combination. This effect is clearly demonstrated in a comparison of the hydroformylation of 1-hexene in the absence and presence of the phthalic acid catalyst modifier. The results are outlined in Equation 2 and 3. A similar result was obtained with 1-decene as the substrate.

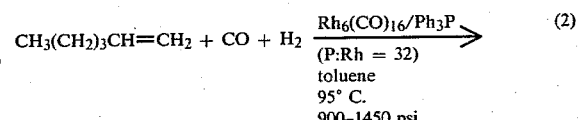

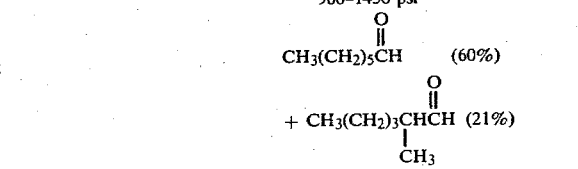

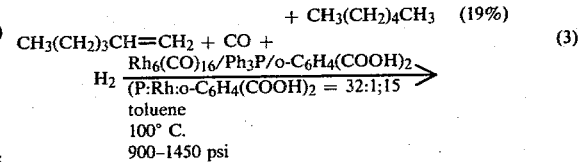

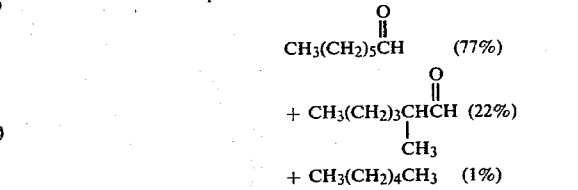

The hydrogenation suppression effect is also operable in the allyl alcohol-oxo tetrahydrofuranylation case. In a controlled comparison as above, the extent of direct propanol formation with and without the phthalic acid co-catalyst is 4% and 21% respectively. If there are no offsetting negative effects of the phthalic acid, the yield of 1,4-butanediol obtainable on hydrolysis-hydrogenation of the intermediate(s) should be correspondingly increased. This has been found qualitatively to be the case.

DESCRIPTION OF THE INVENTION

According to the present invention in its broadest aspects there is provided in a process for preparing oxygenated products by contacting an olefinically unsaturated compound, carbon monoxide and hydrogen with a hydroformylation catalyst, an improvement which comprises adding an acid to the reaction mixture in an amount at least sufficient to suppress hydrogenation of said olefinically unsaturated compound.

In preferred features the acid will have an acid strength at least strong enough to suppress hydrogenation but not so strong as to significantly decompose said oxygenated products. Preferably, the acid will have a $pK_a$ of from about 1.5 to about 5.0 in aqueous solution. More preferably, the acid will be stable, strong and inert with respect to the reactants, and will be selected from organic mono- or polycarboxylic acids, e.g., o-phthalic acid, 4,5-dichlorophthalic acid, or inorganic acids, e.g., phosphoric acid, the like. Special mention is made of o-phthalic acid or phosphoric acid.

Other preferred features of the invention include carrying out the process at a pressure in the range of from about atmospheric to 1500 psi, and especially preferably from 300–1200 psi. Another preferred feature is to carry out the process at a temperature between about 25° C. and 200° C., and especially preferably in the range of 70°–150° C.

Suitable substrates in the present process are any aliphatic or cycloaliphatic compound having at least one ethylenic carbon-to-carbon bond. Thus the reaction is useful for the hydroformylation of olefins having, for example, from 2 to 20 carbon atoms to reaction mixtures comprising aliphatic aldehydes and/or alkanols having one more carbon atom than the starting olefin. The invention is used to advantage in the hydroformylation of carbon-to-carbon ethylenically unsaturated linkages in hydrocarbons. Monoolefins such as ethylene, propylene, butylene, pentenes, hexenes, heptenes, octenes, dodecenes, their homologs, etc., are a few examples of suitable hydrocarbons. Suitable hydrocarbons include both branched- and straight-chain compounds having one or more ethylenic or olefinic sites. These sites may be conjugated, as in 1,3-butadiene, or non-conjugated, as in 1,5-hexadiene. In the case of polyolefins, it is possible to hydroformylate only one or the olefinic sites or all of the sites. The unsaturated carbon-to-carbon olefinic linkages may be between terminal and their adjacent carbon atoms, as in 1-hexene or 1-decene, or between internal chain carbon atoms, as in 4-octene.

Hydroformylation of macromolecular materials involving acyclic units of the above types such as polydiolefinic like polybutadiene as well as copolymers of olefins and diolefins like the styrene-butadiene copolymer, is also contemplated by this invention. Hydrocarbon cyclic compounds, e.g., cyclopentene, cyclohexene, and the like and equally suitable.

Special mention is made of the use of the process to hydroformylate ethylenic carbon-to-carbon linkages of nonhydrocarbons. It is possible to hydroformylate olefinically unsaturated alcohols, aldehydes, acids, esters, and the like, to obtain corresponding alcohols, aldehydes, acids, esters, and the like, containing an aldehyde or hydroxy group on one of the carbon atoms previously involved in the olefinic bond of the starting material.

Illustrative olefinic compounds which can be employed as reactants include ethylene, propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, allyl chloride, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl 7-octenoate, 3-butenic acid, 7-octenoic acid, 3-butenenitrile, 5-hexanamide, acrolein and the like. Preferred olefinic compounds include alkenes, alkyl alkenoates, alkenyl alkanoates, alkenyl alkyl ethers, and alkenols, especially those which contain up to 20 carbon atoms. Preferred olefinic unsaturated compounds are alkenes and/or alkenols of from 2 to 20 carbon atoms. Special mention is made of 1-hexene, 1-decene and allyl alcohol.

Any conventional hydroformylation catalyst known in this art is suitable for the present process. However, it is preferred to use a catalyst comprising a metal selected from rhodium, ruthenium, cobalt, platinum or mixtures of any of the foregoing, alone, or in complex combination with carbon monoxide.

It is also preferred to carry out the process with a catalyst which also includes triorgano-containing ligands such as the trialkylphosphites, the tricycloalkylphosphites, the triarylphosphites, the triarylphosphines, the triarylstibines, and the triarylarsines. Desirably each organo radical in the ligand does not exceed 18 carbon atoms. The triarylphosphites and the triarylphosphines represent the preferred classes of ligands. Specific examples of ligands which are suitable in forming the complex catalysts include trimethylphosphite, triethylphosphite, butyldiethylphosphite, tri-n-propylphosphite, tri-n-butylphosphite, tri-2-ethylhexlphosphite, tri-n-octylphosphite, tri-n-dodecylphosphite, triphenylphosphite, trinaphthylphosphite, triphenylphosphine, tri(p-chlorophenyl) phosphite, tri-naphthylphosphine, phenyl diphenylphosphinite, diphenyl phenylphosphonite, diphenyl ethylphosphonite, triphenylarsine, triphenylstibine, tris(p-chlorophenyl)-phosphine, tri(p-cyanophenyl)phosphite, tri(p-methoxyphenyl)-phosphite, ethyl diphenylphosphinite, and the like.

Especially preferred triorgano ligands comprise a trialkylphosphite, a tricycloalkylphosphite, a triarylphosphite, a triarylphosphine, a triarylstibine, a triarylarsine or a mixture of any of the foregoing. Special mention is made of a catalyst comprising a rhodium carbonyl/triaryl phosphine comples, particularly where triarylphosphine is triphenylphosphine.

The acid employed to suppress hydrocarbon formation can be present during formation of the hydroformylation catalyst, or it can be added after the catalyst is formed, either before or during the addition of the unsaturated olefinic substrate.

The process of this invention may be carried out from about atmospheric pressure up to 10,000 psig or even higher. However, preferably from about 300 psig to 1200 psig will be used. The process may be effected at temperatures ranging from about 10° C. to about 250° C. but, it will be preferably in the range of from about 25° C. to 200° C., and most preferably to the range of from about 70° C. to about 150° C.

The temperature and pressure can be varied within a given reaction so as to improve the efficiency of the hydroformylation of the olefinic starting materials to valuable oxygenated product or products.

The ratio of hydrogen to carbon monoxide employed in the present invention may be varied widely. While mole ratios of hydrogen to carbon monoxide as high as 10 or even higher and as low as 0.1 and even lower may be employed, the preferred ratios are in the range of from about 0.3 to about 2. A more preferable molar ratio of hydrogen to carbon monoxide is in the range of from about 0.8 to about 1.5.

The unsaturated olefinic substrate may also serve as a solvent as well as co-reactant. However, an inert solvent may also be employed to advantage in the disclosed process. For example, a wide variety of solvents, e.g., aromatic and aliphatic hydrocarbons, esters, ethers, nitriles, halogenated hydrocarbons and the like, including benzene, hexene, toluene, mesitylene, xylene, cyclohexane, ethyl acetate, tetrahydrofuran, chlorobenzene, methylene chloride, acetonitrile and the like and mixtures thereof may be employed.

The process may be carried out batchwise or on a continuous or semicontinuous basis. Typically in a continuous or semicontinuous process, the unsaturated organic compound is supplied to a reactor in which the temperature and pressure conditions for reaction are already established. The reactor will also contain the solvent and the catalyst. The products can be isolated by distillation, and the catalyst can be recycled to the reactor in the distillation residue.

Such techniques are well known to those of ordinary skill in the art.

DESCRIPTION OF THE PREFERRED EMBODIMENTS

The following examples are set forth to illustrate the present invention. They are not to be construed to limit the claims in any manner whatsoever.

EXAMPLE 1

Hydroformylation of 1-Hexene in the Presence of o-Phthalic Acid

A 300 cc Autoclave Engineers Magnedrive autoclave is charged with 50.0 grams of 1-hexane (594 mmol), 9.6 grams of triphenylphosphine (36.6 mmol), 2.9 grams of o-phthalic acid (17.5 mmol), 0.201 grams of hexarhodium hexadecacarbonyl (0.189 mmol, 1.13 meq Rh), and 75 ml of toluene. The mixture is subjected to 1450 psi of 2:1 $H_2/CO$ and heated to 100° C., the temperature at which the exothermic reaction is self-sustaining. Gas is taken up and replenished (1:1 $H_2/CO$) at 900–1450 psi. In 30 minutes at 100° C. total gas uptake corresponds to 2700 psi. Quantitative VPC analysis of the reaction products shows the presence of 48.3 grams of n-heptanal (77% yield), 13.2 grams of 2-methylhexanal (22% yield), and about 0.5 grams of hexane (1% yield). In a duplicate experiment, the yields of these three products are 74%, 25% and 1%, respectively.

Comparative Procedure A

Hydroformylation of 1-Hexene in Absence of o-Phthalic Acid

The procedure outlined above is followed, but with omission of the o-phthalic acid catalyst component. The exothermic reaction is self-sustaining at 95° C. in this case. Quantitative VPC analysis of the reaction products shows the presence of 40.7 grams of n-heptanal (60% yield), 14.2 grams of 2-methylhexanal (21% yield), and 9.7 grams of hexane (19% yield). In a duplicate experiment the yields of these three products are 64%, 18% and 18%, respectively.

It can be seen that the presence of o-phthalic acid markedly suppresses double-bond hydrogenation.

EXAMPLE 2

Hydroformylation of 1-Decene in the Presence of o-Phthalic Acid

Example 1 is repeated with 50.0 grams of 1-decene (356 mmol) substituted for the 1-hexene, and using o-phthalic acid according to this invention. Analysis of the products of the reaction shows the presence of 38.1 grams of n-undecanal (63% yield), 7.9 grams of 2-methyl-decanal (13% yield), 10.5 grams of what is tentatively identified as 2-decene (on the basis of its ir and mass spectra) (21% yield), and only 1.6 grams of decane (3% yield).

Comparative Procedure B

Hydroformylation of 1-Decene in Absence of o-Phthalic Acid

The procedure of Example 2 is repeated, omitting the o-phthatic acid. The products in this case are 41.4 grams of n-undecanal (68% yield), 12.9 grams of 2-methyldecanal (21% yield), and 5.5 grams of decane (11% yield).

Again, it can be seen that the presence of o-phthalic acid markedly suppresses double-bond hydrogenation.

EXAMPLE 3

Hydroformylation/Tetrahydrofuranylization of Allyl Alcohol in Presence of o-Phthalic Acid The autoclave is charged with 50.0 grams of allyl alcohol (861 mmol), 9.6 grams of triphenylphosphine (36.6 mmol), 2.9 grams of o-phthalic acid (17.5 mmol), 0.201 grams of hexarhodium hexadecacarbonyl (0.189 mmol, 1.13 meq Rh), and 75.0 grams of methanol (2.34 mole). The mixture is subjected to 1350 psi of 2:1 $H_2/CO$ and heated at 105° C. for 30 minutes, with gas taken up and replenished (1:1 $H_2/CO$) at 700–1350 psi. Direct VPC analysis of the reaction products shows that 2-methoxytetrahydrofuran is the major product and that only 2.2 grams of n-propanol (4% yield) is formed.

Comparative Procedure C

Hydroformylation/Tetrahydrofuranylization of Allyl Alcohol in Absence of o-Phthalic Acid For purposes of comparison the procedure of Example 3 is repeated, but with omission of the o-phthalic acid. Gas uptake is sustained in this case at 90° C. Direct VPC analysis of the products shows that presence of a smaller amount of 2-methoxytetrahydrofuran, the branched oxo product 2-(hydroxymethyl)propionaldehyde, and several other higher- and lower-boiling components.

Phthalic acid has a $pK_a$ of 2.89($K_1$), and a dissociation constant of $1.3 \times 10^{-3}$ in aqueous solution. This level of acid strength is preferred for the co-catalysis function as described.

Obviously, minor variations will suggest themselves to those skilled in the art in view of the above-identified description. For example, if other olefinic substrates such as alkenes, methacrylate esters and styrene are employed, by-product formation due to olefinic hydrogenation will be suppressed. Moreover, substituted phthalic acids or other dicarboxylic acid and their derivatives, esters and half esters of phthalic acid, metal phthalates, di-phthalate salts, phthalic anhydrides and related anhydrides will be useful. All such obvious modifications are within the full intended scope of the appended claims.

I claim:

1. In a process for preparing aldehydes and alcohols by contacting an olefinically unsaturated compound having two to twenty carbon atoms, carbon monoxide and hydrogen with a hydroformylation catalyst, the improvement which comprises adding an acidic compound selected from the group consisting of mono- and polycarboxylic acids and inorganic acids to the reaction mixture in an amount at least sufficient to suppress hydrogenation of said olefinically unsaturated compound, said acidic compound having an acid strength at least strong enough to suppress hydrogenation but not so strong as to significantly decompose said aldehyde and alcohol products and sufficient to provide a pKa of from about 1.5 to about 5.0, and carrying out said reaction at a pressure in the range from atmospheric to 10,000 psig and a temperature in the range from about 10° to about 250° C.

2. A process as defined in claim 1 wherein said acid is o-phthalic acid.

3. A process as defined in claim 1 wherein said acid is phosphoric acid.

4. A process as defined in claim 1 carried out at a pressure in the range of 300–1200 psi.

5. A process as defined in claim 1 carried out at a temperature between about 25° C. and 200° C.

6. A process as defined in claim 5 carried out at a temperature in the range of 70°–150° C.

7. A process as defined in claim 1 wherein said olefinically unsaturated compound is selected from an alkene, an alkyl alkenoate, an alkenyl alkanoate, an alkenyl alkyl ether, an alkenol, or a mixture of any of the foregoing.

8. A process as defined in claim 7 wherein said olefinically unsaturated compound is an alkene of from 2 to 20 carbon atoms.

9. A process as defined in claim 8 wherein said alkene is 1-hexene.

10. A process as defined in claim 8 wherein said alkene is 1-decene.

11. A process as defined in claim 7 wherein said olefinically unsaturated compound is an alkenol of from 3 to 20 carbon atoms.

12. A process as defined in claim 11 wherein said alkenol is allyl alcohol.

13. A process as defined in claim 1 wherein said catalyst comprises a metal selected from rhodium, ruthenium, cobalt, platinum or mixtures of any of the foregoing, alone, or in complex combination with carbon monoxide.

14. A process as defined in claim 13 wherein said catalyst also includes a triorgano-containing ligand.

15. A process as defined in claim 14 wherein said triorgano-containing ligand comprises a trialkylphosphite, a tricycloalkylphosphite, a triarylphosphite, a triarylphosphine, a triarylstibine, a triarylarsine or a mixture of any of the foregoing.

16. A process as defined in claim 14 wherein said catalyst comprises a rhodium carbonyl/triaryl phosphine complex.

17. A process as defined in claim 16 wherein said triarylphosphine is triphenylphosphine.

18. In a process for preparing aldehydes and alcohols by contacting (1) an olefinically unsaturated compound selected from among alkenes, alkyl alkenoates, alkenyl alkanoates, alkenyl alkyl ethers, alkenols and mixtures thereof, said compounds having two to 20 carbon atoms, (2) carbon monoxide and (3) hydrogen with (4) a hydroformylation catalyst comprising a metal selected from rhodium, ruthenium, cobalt, platinum or mixtures of any of these, alone, or in complex combination with carbon monoxide, wherein the mole ratio of hydrogen to carbon monoxide is in the range of from 0.1 to 10, at a temperature between about 25° C., and 200° C., and a pressure in the range of 300–1200 psi, the improvement comprising adding an acidic compound selected from the group consisting of phthalic acid and related compounds and phosphoric acid, in an amount at least sufficient to suppress hydrogenation of the olefinically unsaturated compound but not significantly decompose the product aldehydes and alcohols, said acidic compound being sufficient to provide a pKa of from about 1.5 to about 5.0.

* * * * *